(12) United States Patent
Swick

(10) Patent No.: US 7,217,252 B2
(45) Date of Patent: May 15, 2007

(54) APPLICATOR DEVICE FOR MEDICATED MATERIALS

(75) Inventor: Paul B. Swick, Lebanon, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 260 days.

(21) Appl. No.: 10/806,947

(22) Filed: Mar. 23, 2004

(65) Prior Publication Data
US 2004/0249352 A1 Dec. 9, 2004

Related U.S. Application Data

(63) Continuation-in-part of application No. 10/366,710, filed on Feb. 12, 2003, which is a continuation-in-part of application No. 10/172,729, filed on Jun. 14, 2002, now Pat. No. 7,104,968.

(51) Int. Cl.
*A61M 31/00* (2006.01)
*A61F 13/20* (2006.01)

(52) U.S. Cl. .................... 604/60; 604/279; 604/15; 604/57

(58) Field of Classification Search ............ 604/57–60, 604/73, 93.01, 104–109, 171–172, 181, 187, 604/218, 220, 264, 279, 285–286, 288, 328, 604/330, 11–16, 904
See application file for complete search history.

(56) References Cited

U.S. PATENT DOCUMENTS

| | | | |
|---|---|---|---|
| 2,007,626 A | 7/1935 | Waring | |
| 2,754,822 A | 7/1956 | Emelock | |
| 3,297,031 A | 1/1967 | Bray | |
| 3,424,158 A | 1/1969 | Silver | |
| 3,667,465 A | 6/1972 | Voss | |
| 3,884,233 A | 5/1975 | Summey | |
| 3,934,584 A | 1/1976 | Corio | |
| 4,318,405 A | 3/1982 | Sneider | |
| 4,341,211 A | 7/1982 | Kline | |
| 4,361,150 A | 11/1982 | Voss | |
| 4,421,504 A | 12/1983 | Kline | |
| 4,496,341 A | 1/1985 | Brucks | |
| 4,536,178 A | 8/1985 | Lichstein et al. | |
| 4,543,086 A | 9/1985 | Johnson | |

(Continued)

FOREIGN PATENT DOCUMENTS

EP 1 371 386 A3 12/2003

(Continued)

*Primary Examiner*—Catherine S. Williams

(57) ABSTRACT

A device for delivering a medicated product into a bodily cavity includes a barrel member having a dispensing end, a proximal end, which is positioned opposite the dispensing end, and a bore, which extends through the barrel member. The bore is sized and shaped so as to receive a medicated product therein and includes an opening formed in the dispensing end of the barrel member. The opening is sized and shaped so as to permit a medicated product received in the bore to be dispensed therethrough. The applicator is also provided with a plunger member movably extending through the bore of the barrel member for dispending a medicated product from the bore through the opening. The barrel member includes at least one substantially flexible section located between the dispending end and the proximal end such that the barrel member is bendable about the flexible section.

20 Claims, 12 Drawing Sheets

U.S. PATENT DOCUMENTS

| | | | |
|---|---|---|---|
| 4,563,182 A | 1/1986 | Stoy et al. | |
| 4,588,395 A | 5/1986 | Lemelson | |
| 4,620,534 A | 11/1986 | Zartman | |
| 4,645,488 A | 2/1987 | Matukas | |
| 4,900,315 A | 2/1990 | Lundqvist et al. | |
| 4,990,136 A | 2/1991 | Geria | |
| D320,084 S | 9/1991 | Stewart et al. | |
| 5,087,239 A | 2/1992 | Beastall et al. | |
| 5,201,779 A | 4/1993 | Shiao | |
| 5,213,566 A | 5/1993 | Weissenburger | |
| 5,330,427 A | 7/1994 | Weissenburger | |
| 5,397,312 A | 3/1995 | Rademaker et al. | |
| 5,404,870 A | 4/1995 | Brinkerhoff et al. | |
| 5,437,628 A | 8/1995 | Fox et al. | |
| 5,656,283 A | 8/1997 | Brummer et al. | |
| 5,662,601 A | 9/1997 | Snead | |
| 5,788,664 A | 8/1998 | Scalise | |
| 5,807,372 A | 9/1998 | Balzar | |
| 5,860,946 A | 1/1999 | Hofstatter | |
| 6,019,743 A * | 2/2000 | Cole et al. | 604/15 |
| 6,027,471 A | 2/2000 | Fallon et al. | |
| D436,661 S | 1/2001 | Berry | |
| 6,168,576 B1 | 1/2001 | Reynolds | |
| 6,190,348 B1 | 2/2001 | Tiemann et al. | |
| D445,176 S | 7/2001 | Landers | |
| 6,368,300 B1 | 4/2002 | Fallon et al. | |
| 6,432,075 B1 | 8/2002 | Wada et al. | |
| 2002/0177582 A1 | 11/2002 | Maloney | |
| 2003/0233077 A1 | 12/2003 | Swick | |
| 2003/0233078 A1 | 12/2003 | Swick | |

FOREIGN PATENT DOCUMENTS

| | | |
|---|---|---|
| FR | 2610831 | 8/1988 |
| GB | 956679 | 4/1964 |
| GB | 2097259 | 11/1982 |
| WO | WO 00/66213 A1 | 11/2000 |

* cited by examiner

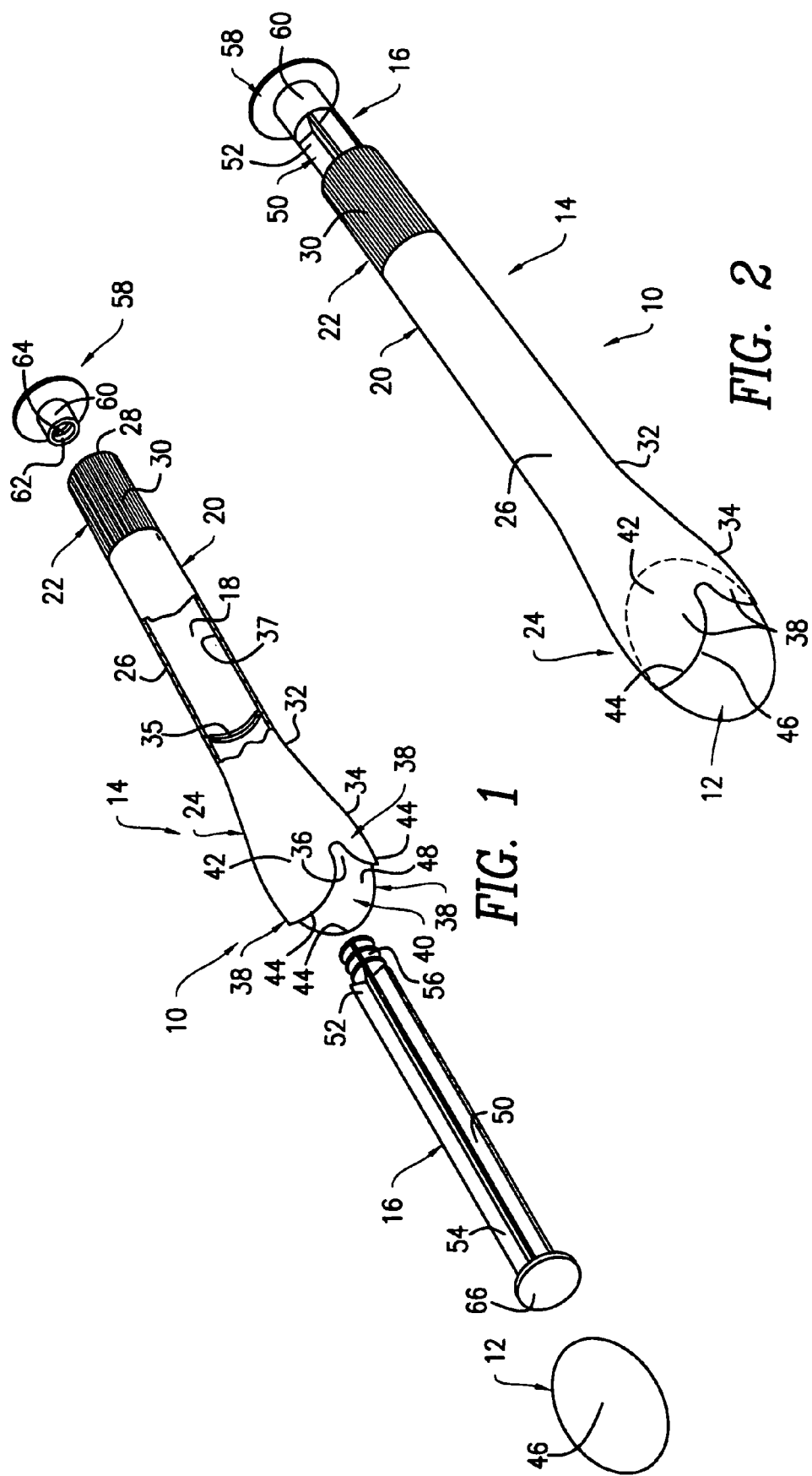

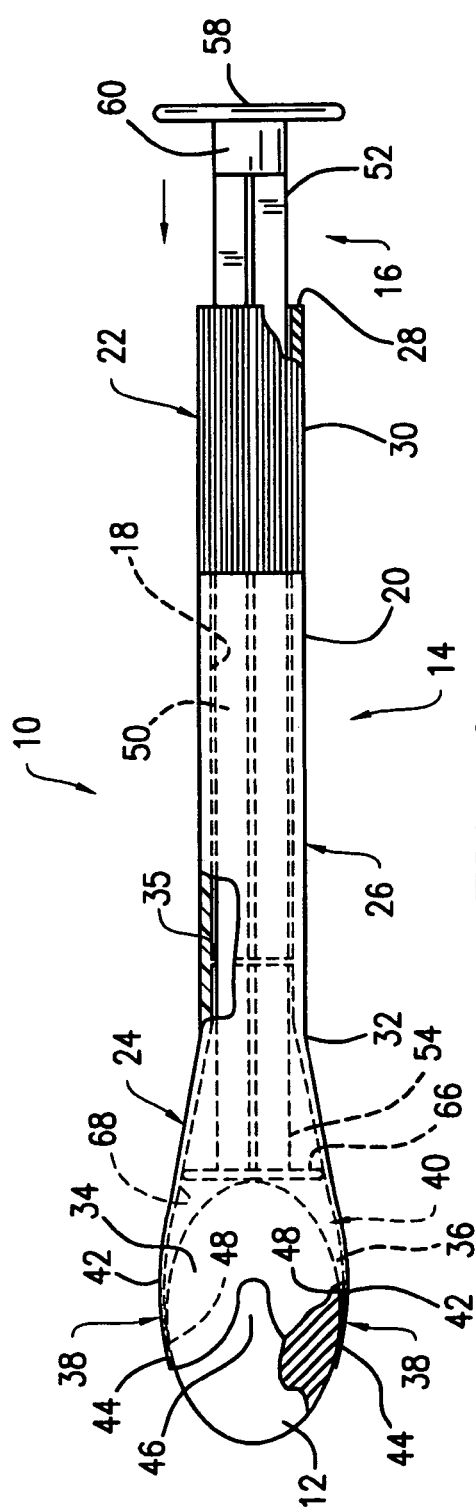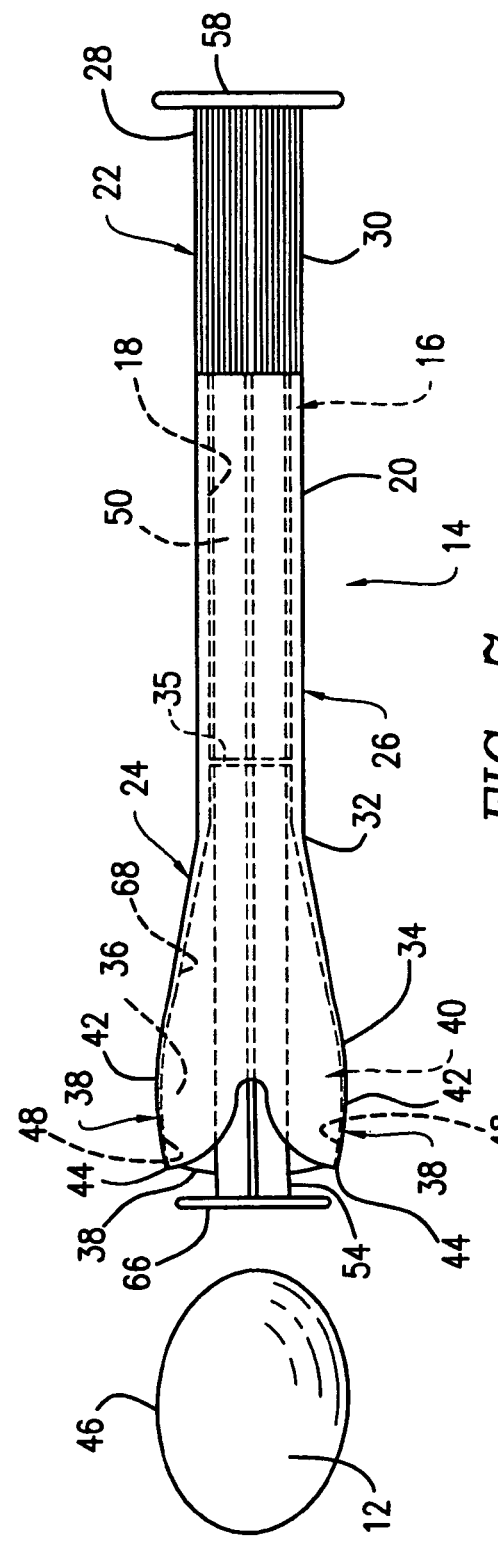
FIG. 6
FIG. 7

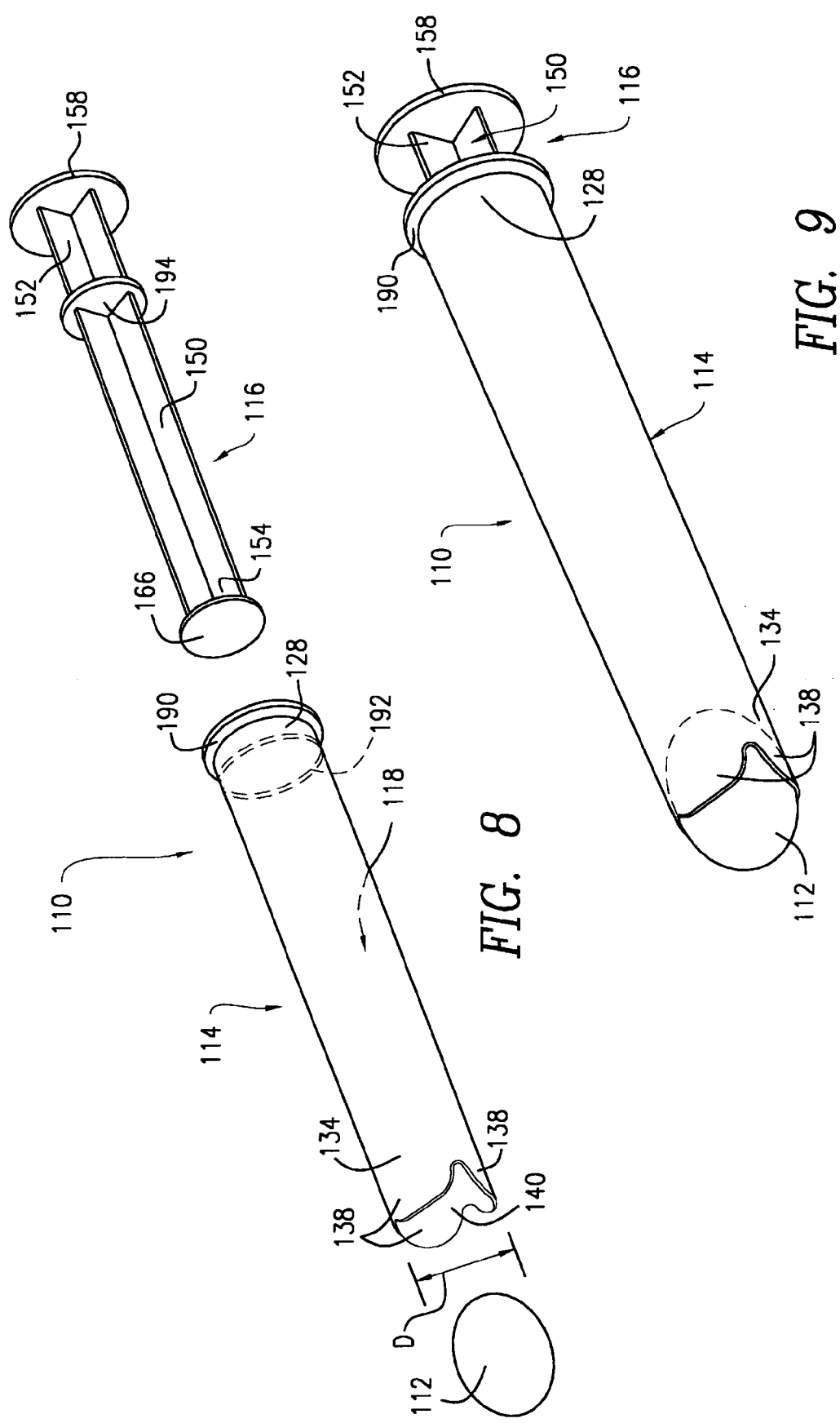

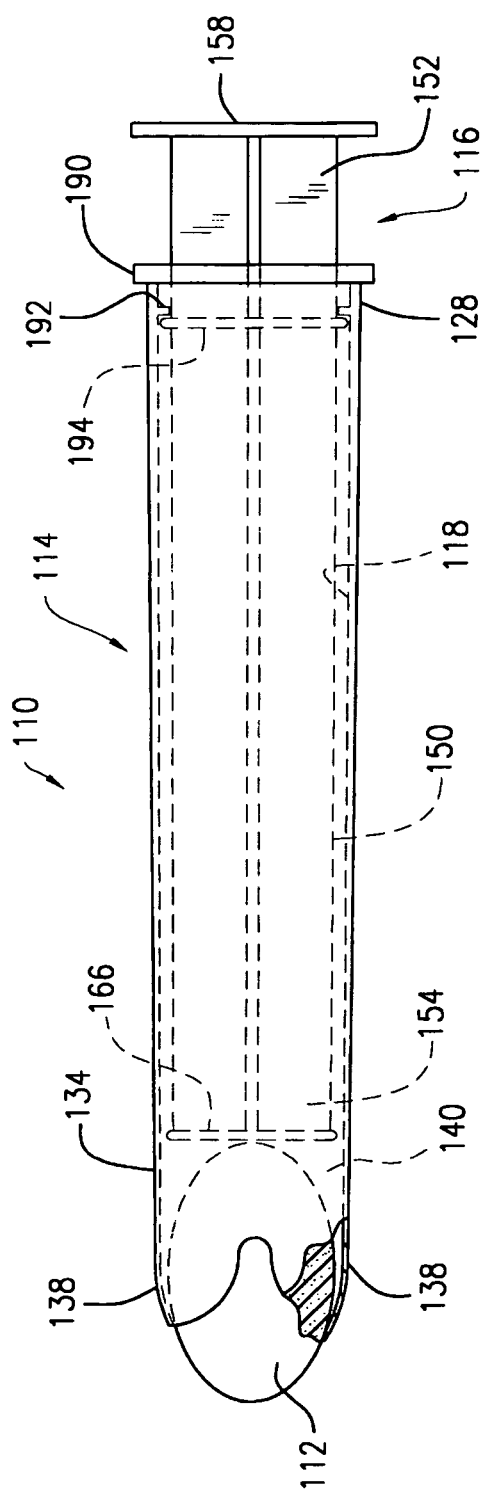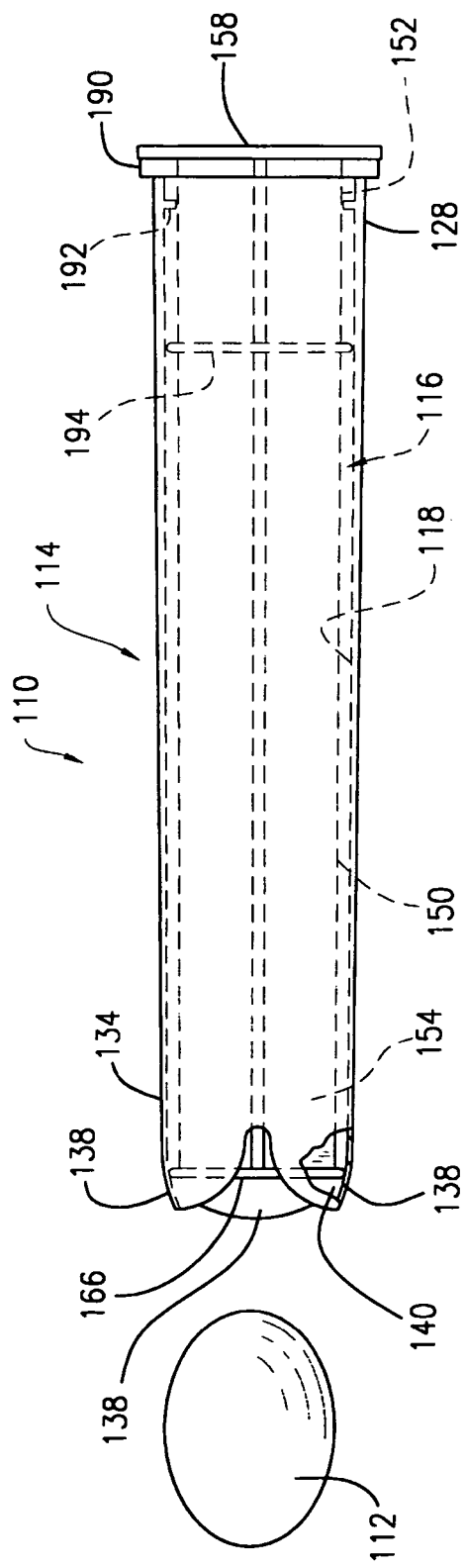
FIG. 12
FIG. 13

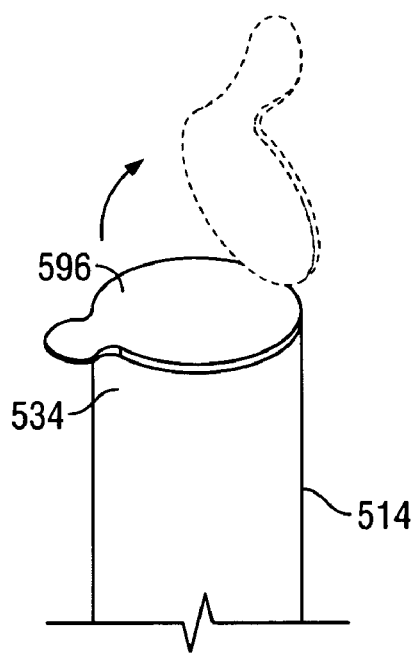
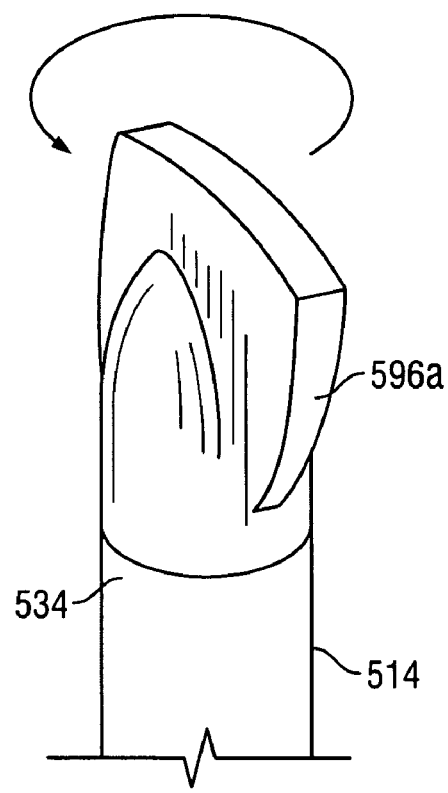
FIG. 18A    FIG. 18B
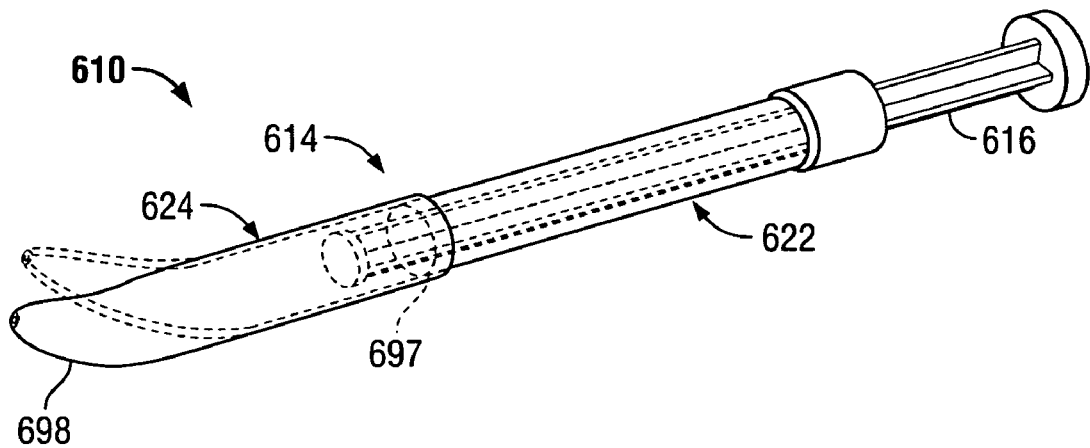
FIG. 19

US 7,217,252 B2

APPLICATOR DEVICE FOR MEDICATED MATERIALS

CROSS-REFERENCE TO RELATED APPLICATIONS

This is a continuation-in-part of U.S. patent application Ser. No. 10/366,710, filed Feb. 12, 2003, which is a continuation-in-part of U.S. patent application Ser. No. 10/172,729, filed Jun. 14, 2002 now U.S. Pat. No. 7,104,968. The disclosures of U.S. patent application Ser. Nos. 10/172,729 and 10/366,710 are incorporated herein by reference.

FIELD OF THE INVENTION

The present invention relates to applicator devices for medicated materials and, more particularly, to an applicator device adapted for depositing medicated materials in a bodily cavity or passage.

BACKGROUND OF THE INVENTION

Applicators have been in use for delivering medicated materials (e.g., suppositories, creams and ointments) to bodily cavities, such as vaginal canals and recta. Conventional applicators are equipped with barrel members for receiving medicated materials and plunger members for expelling same from the barrel members into bodily cavities.

The barrel members of some applicators include loading ends which are typically equipped with finger-like members or segments projecting therefrom for releasably attaching suppositories to the loading ends (see, for instance, U.S. Pat. Nos. 2,754,822; 3,667,465; 3,934,584; 4,361,150; 5,201,779; 5,404,870; and 5,860,946). The finger-like members are sized such that, when suppositories are loaded onto the loading ends, they are enclosed substantially entirely by the finger-like members.

The suppository applicators discussed above have various disadvantages. For instance, suppositories, when exposed to moisture, tend to stick to surfaces that are in contact therewith. In such circumstances, when the applicators are exposed to relatively high humidity, suppositories loaded therein tend to stick to the loading ends of the applicators. Because the suppositories are enclosed substantially entirely by the finger-like members, they have a relatively large area of contact with the loading ends of the applicators. As a result, when the suppositories stick to the applicators during storage or use, it becomes difficult to expel same from the applicators.

In addition to the disadvantages discussed above, conventional applicators are substantially rigid such that they do not easily conform to natural curves of the bodily cavities to which they are inserted. As a result, rigid conventional applicators can cause discomfort to their users.

In the foregoing circumstances, there is a need for an improved applicator device overcoming the disadvantages and shortcomings discussed above.

SUMMARY OF THE INVENTION

The present invention overcomes the disadvantages and shortcomings discussed above by providing an improved applicator device for delivering pharmaceutical products or the like to a bodily cavity. More particularly, the device includes a barrel member having a distal end which is equipped with an opening. The applicator also includes a plurality of petals extending outwardly from the distal end in a generally axial direction. The petals cooperate with the opening so as to form a receptacle for releasably receiving a pharmaceutical product in the distal end of the barrel member. Each of the petals has a truncated flexible tip sized and shaped so as to engage a substantially central portion of the pharmaceutical product such that a large section of the pharmaceutical product extends outwardly beyond the petals so as to facilitate the release of the pharmaceutical product from the receptacle. The device also includes a plunger member for releasing the pharmaceutical product from the receptacle. In accordance with the present invention, the device can be packaged in a package together with the pharmaceutical product received in the receptacle.

In accordance with an alternate embodiment of the present invention, a device for delivering a medicated product into a bodily cavity includes a barrel member having a dispensing end, a proximal end, which is positioned opposite the dispensing end, and a bore, which extends through the barrel member. The bore is sized and shaped so as to receive a medicated product therein and includes an opening formed in the dispensing end of the barrel member. The opening is sized and shaped so as to permit a medicated product received in the bore to be dispensed therethrough. The applicator is also provided with a plunger member movably extending through the bore of the barrel member for dispending a medicated product from the bore through the opening. The barrel member includes at least one substantially flexible section located between the dispending end and the proximal end such that the barrel member is bendable about the flexible section.

BRIEF DESCRIPTION OF THE DRAWINGS

For a more complete understanding of the present invention, reference is made to the following detailed description of the present invention considered in conjunction with the accompanying drawings, in which:

FIG. 1 is an exploded perspective view of a suppository applicator constructed in accordance with a first exemplary embodiment of the present invention;

FIG. 2 is a perspective view of the applicator of FIG. 1 in an assembled configuration ready for use;

FIGS. 6 and 7 are side elevational views of the applicator shown in FIGS. 1, 2 and 5, illustrating its operation;

FIG. 8 is an exploded perspective view of a suppository applicator constructed in accordance with a second exemplary embodiment of the present invention;

FIG. 9 is a perspective view of the applicator of FIG. 8 in an assembled configuration ready for use;

FIGS. 12 and 13 are side elevational views of the applicator shown in FIGS. 8 and 9, illustrating its operation;

FIG. 18A is an enlarged perspective view of a sealed end of the applicator shown in FIG. 18;

FIG. 18B is a perspective view of a modified version of the sealed end of the applicator shown in FIG. 18A; and FIG. 19 is a perspective view of an applicator constructed in accordance with a seventh embodiment of the present invention.

DETAILED DESCRIPTION OF THE EXEMPLARY EMBODIMENTS

Figure 5:
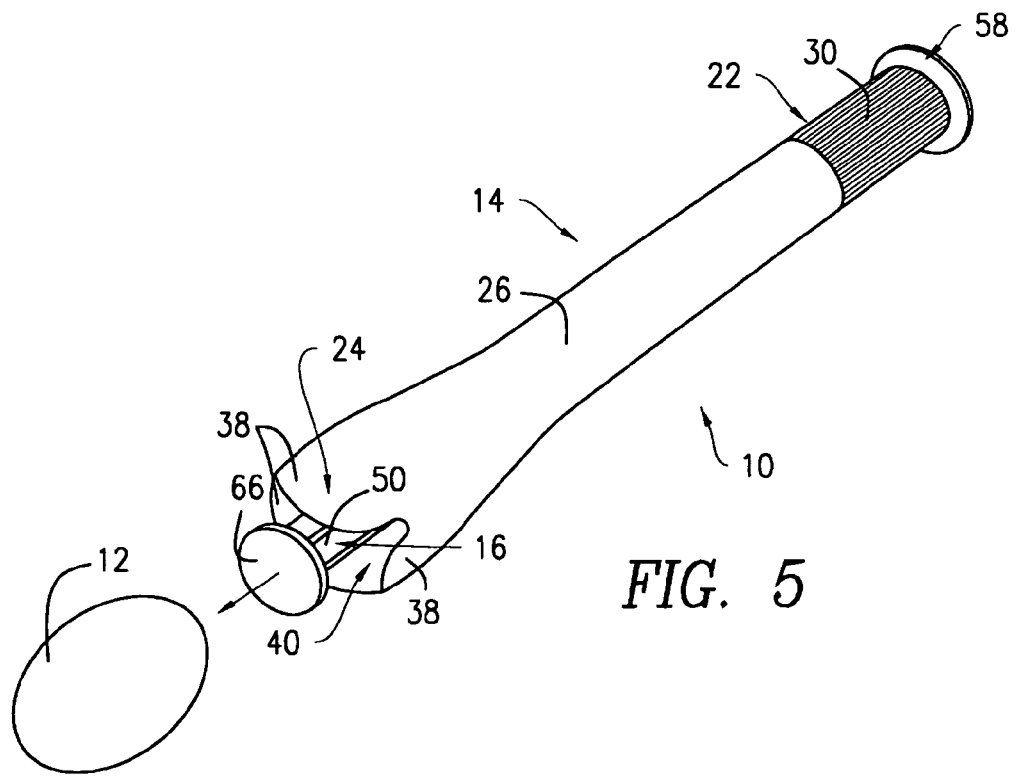
FIG. 5 is a perspective view of the applicator of FIG. 2 illustrating the dispensing of a suppository product.

Referring to FIGS. 1, 2 and 5, there is shown a suppository applicator 10 constructed in accordance with a first embodiment of the present invention. More particularly, the applicator 10 is adapted for use in depositing an oval-shaped suppository product 12 in a bodily cavity, such as a vaginal cavity, a rectum, etc. The applicator 10 includes a barrel member 14 and a plunger member 16 extending through the barrel member 14. The barrel member 14 and the plunger member 16 are made from a suitable material (e.g., thermoplastics, polyolefins, polyolefin copolymers, modified polyvinyl chloride, thermoplastic rubber compounds, polyurethanes, etc.) preferably by a conventional injection molding process. Alternatively, one or both of the barrel member 14 and the plunger member 16 can be made by using other conventional processes.

Now referring to FIGS. 1, 2 and 5–7, the barrel member 14 is provided with an interior passageway 18 extending therethrough. The barrel member 14, which has a unitary construction and an annular wall 20 defining the passageway 18, is provided with a proximal section 22, a distal section 24 and an intermediate section 26. The intermediate section 26 is located between the proximal and distal sections 22, 24. The proximal section 22 includes an open end 28, as well as a ribbed surface 30 so as to provide a gripping surface during the use of the applicator 10. The distal section 24 has a proximal end 32, which is connected to the intermediate section 26, and a distal end 34 opposite to the proximal end 32. The distal section 24 has a flaring construction (i.e., the diameter of the proximal end 32 is smaller than the diameter of the distal end 34) and has an opening 36 formed therein and communicating with the passageway 18.

An annular ring or projection 35 (see FIGS. 1, 6 and 7) is formed on the intermediate section 26 adjacent to the proximal end 32 of the distal section 24 for purposes to be discussed hereinafter. More particularly, the annular ring 35 projects radially inwardly from an inner surface 37 (see FIG. 1) of the wall 20 into the passageway 18 of the barrel member 14. The annular ring 35 can be formed integrally with the wall 20 or can be formed as a member discrete and separate from the wall 20.

The distal section 24 of the applicator 10 is provided with three flexible, truncated petals 38 (see FIGS. 1, 2 and 5–7) encircling the opening 36 and extending outwardly therefrom in a direction generally parallel to the longitudinal axis of the barrel member 14 (referred to hereinafter as "the axial direction"). The petals 38 cooperate with the opening 36 and the distal section 24 so as to form a receptacle 40 for releasably receiving the suppository product 12 therein. Each of the petals 38 is provided with a generally semi-circular shape and has a base 42, which is integrally connected to the distal end 34 of the distal section 24, and a tip 44, which is located opposite the base 42. Due to its truncated construction, each of the petals 38 has an axial length sufficient to securely retain the suppository product 12 within the receptacle 40, but short enough to create a minimal frictional resistance to the suppository product 12 during its dispensing from the receptacle 40. With reference to FIG. 6, the petals 38 are sized and shaped such that, when the suppository product 12 is received in the receptacle 40, the tips 44 of the petals 38 engage a substantially central portion 46 of the suppository product 12 (e.g., the tips 44 are adapted to engage a portion of the suppository product 12 located slightly outwardly in the axial direction from the central portion 46 of the suppository product 12). By way of example, each of the petals 38 can have an axial length which is substantially equal to one half of the width of the suppository product 12 measured along its major axis. As a result, a substantial part of the suppository product 12 (e.g., an approximately half of the suppository product 12) extends axially beyond the receptacle 40 to facilitate easy unloading of the suppository product 12 from the receptacle 40.

Now referring to FIGS. 1, 6 and 7, each of the petals 38 is provided with a concave interior surface 48 which corresponds generally to the contour of the central portion 46 of the suppository product 12. More particularly, each of the petals 38 curves slightly inwardly in a generally radial direction as it extends from its base 42 to its tip 44 so as to engage and retain the suppository product 12 in the receptacle 40 (see FIG. 6). In this manner, even if a large part of the suppository product 12 extends beyond the tips 44 of the petals 38, the petals 38 cooperate with one another so as to retain the suppository product 12 in the receptacle 40. Additionally, the tips 44 of the petals 38 form a second opening that maintains a larger diameter than a smallest inner diameter along the length of the barrel member 14 or the diameter at the intermediate section 26 at the interface of the proximal section 22 and the distal section 24 both before and after release of the suppository product 12, as shown in FIGS. 6 and 7.

With reference to FIG. 6, the barrel member 14 is also constructed such that the thickness of the wall 20 at the distal section 24, and more specifically at the tips 44 of the petals 38, is significantly smaller than the thickness of the wall 20 at the proximal section 22. In this manner, the petals 38 are provided with a sufficient flexibility and resiliency such that the petal tips 44 are expandable radially outwardly and contractible radially inwardly so as to permit easy loading and unloading of the suppository product 12.

Referring back to FIGS. 1, 2 and 5–7, the plunger member 16 includes a ribbed shaft 50 having a proximal end 52 and a distal end 54 and movably received in the passageway 18 of the barrel member 14. The proximal end 52 of the shaft 50 has beads 56 (see FIG. 1). A thumb platform 58 is also formed on the proximal end 52 of the shaft 50 and has a centrally positioned mounting tab 60. The mounting tab 60 has a female receptacle opening 62 (see FIG. 1) having beads 64 adapted to engage the beads 56 of the shaft 50 such that the proximal end 52 of the shaft 50 can be snap-fitted into the receptacle opening 62 of the thumb platform 58. In this manner, the thumb platform 58 is securely attached to the shaft 50 by an interference fit. A contact platform 66 is integrally formed with the distal end 54 of the shaft 50. The contact platform 66 is sized and shaped so to be received movably in the receptacle 40 of the distal section 24 of the barrel member 14 for use in discharging the suppository product 12 from the applicator 10. In this regard, the contact platform 66 has an oversized shape (i.e., has a diameter similar or substantially identical to the width of the suppository product 12 measured along its minor axis) for purposes to be discussed hereinafter.

With reference to FIGS. 2 and 5–7, the plunger member 16 is movable relative to the barrel member 14 in the axial direction between a retracted position (see FIGS. 2 and 6), in which the contact platform 66 is positioned adjacent the proximal end 32 of the distal section 24 of the barrel member 14, and an extended position (see FIGS. 5 and 7), in which the contact platform 66 is located axially outwardly from the tips 44 of the petals 38 and hence the receptacle 40. In this regard, the outer diameter of the thumb platform 58 is greater than that of the proximal section 22 of the barrel member 14 so as to prevent the plunger member 16 from moving beyond its extended position (see FIG. 7). Similarly, the outer diameter of the contact platform 66 is larger than the inner diameter of the proximal end 32 of the distal section 24 such that the contact platform 66 engages an interior portion 68 (see FIG. 6) of the distal section 24 located adjacent to the proximal end 32, thereby inhibiting the plunger member 16 from moving beyond its retracted position. When the plunger member 16 is positioned in its retracted position, the contact platform 66 abuts an end of the suppository product 12 (see FIG. 6) so as to prevent it from being positioned too far into the receptacle 40. More particularly, the contact platform 66 ensures that the suppository product 12 is cradled in the receptacle 40 in a preferred holding position, in which it is engaged by the distal section 24 of the barrel member 14 only at the tips 44 of the petals 38, thereby minimizing the area of contact between the suppository product 12 and the barrel member 14. In this regard, the receptacle 40 preferably has a size which is greater than that of the suppository product 12 such that the entire interior surface of the receptacle 40, with the exception of the tips 44 of the petals 38, is out of contact with the suppository product 12, whereby the suppository product 12 can be released easily from the receptacle 40.

With reference to FIGS. 1, 6 and 7, the annular ring 35, which is formed in the passageway 18 of the barrel member 14, is sized and shaped such that the shaft 50 movably extends through the annular ring 35. The annular ring 35 is adapted to slidably grip the shaft 50 so as to create a frictional fit between the barrel member 14 and the plunger member 16. That is, the shaft 50 is constantly engaged by the annular ring 35 throughout its movement between the extended and retracted positions and is thereby held in position by the annular ring 35. In this manner, the shaft 50 and therefore the plunger member 16 are inhibited from moving freely and causing interference during the use of the applicator 10. In an alternate embodiment, the annular ring 35 can be eliminated, thereby permitting free movement of the plunger member 16.

Referring back to FIG. 1, the applicator 10 is assembled by inserting the shaft 50 into the passageway 18 through the opening 36 of the distal section 24 such that its proximal end 52 is extended outwardly from the open end 28 of the barrel member 14. The thumb platform 58 is then attached to the proximal end 52 of the shaft 50. The suppository product 12 is then inserted into the receptacle 40 of the applicator 10 for delivery into a bodily cavity.

Figure 3:
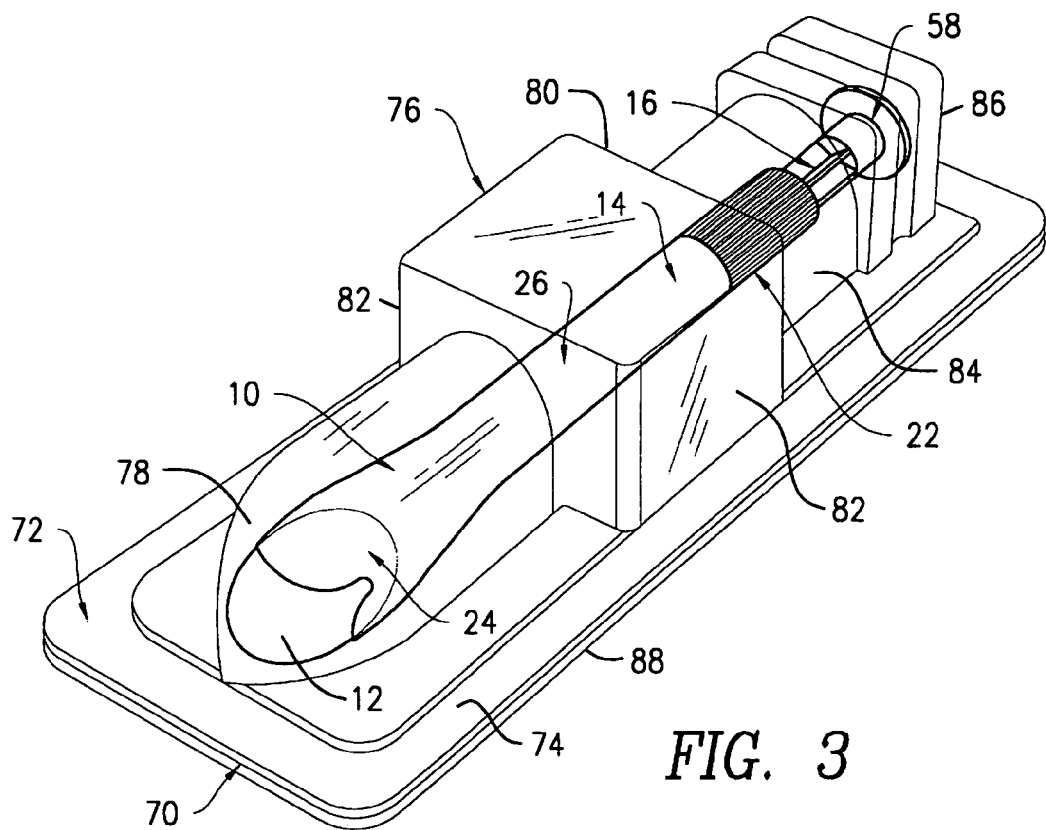
FIG. 3 is a perspective view of the applicator of FIG. 2 packaged in a blister packaging assembly.
Figure 4:
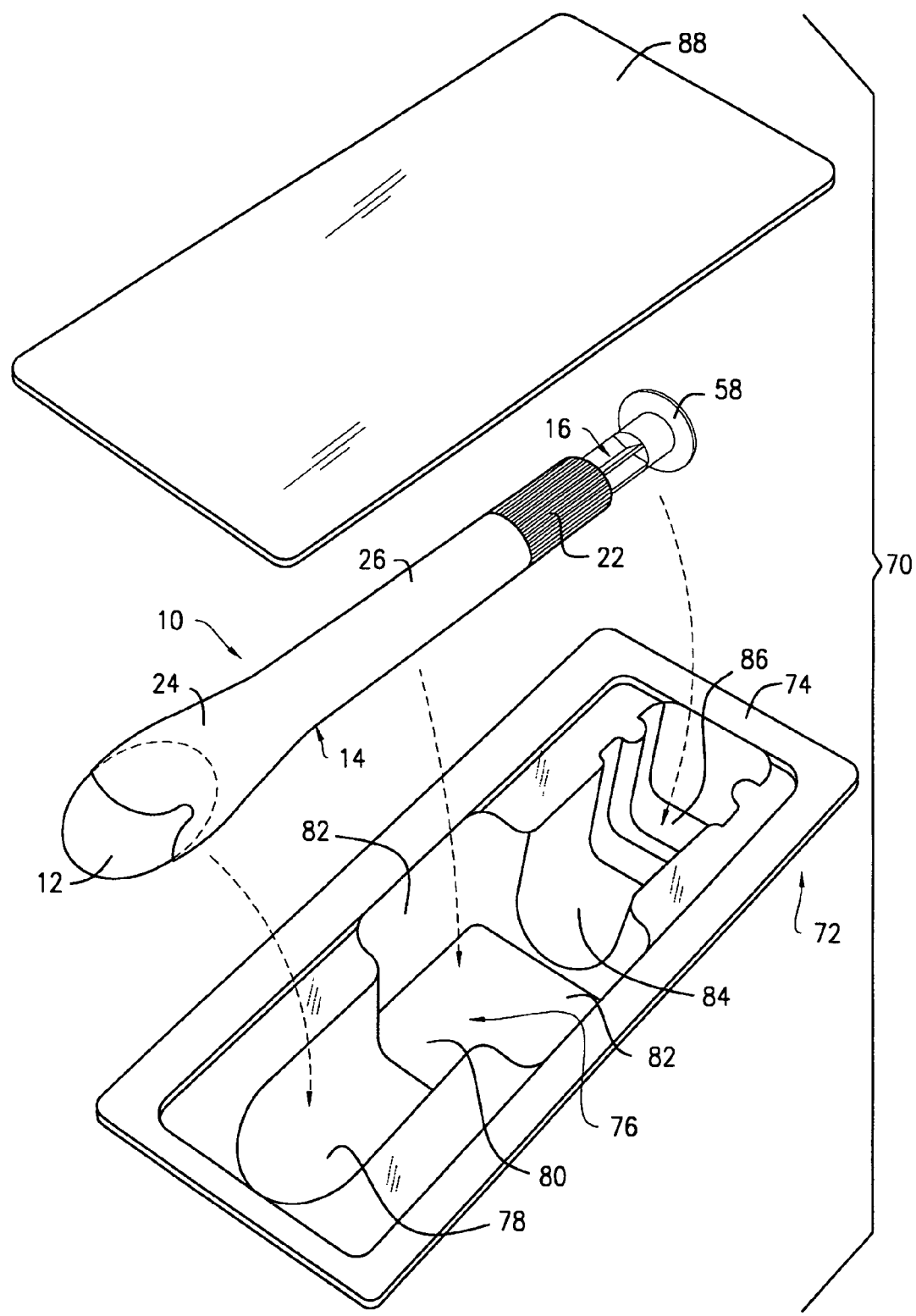
FIG. 4 is an exploded perspective view of the blister packaging assembly of FIG. 3.

The applicator 10 can be provided to a user without the suppository product 12 pre-installed in the receptacle 40. Alternatively, the applicator 10 can be provided to a user with the suppository product 12 pre-filled in the receptacle 40. When provided in its pre-filled form, the applicator 10 can be packaged in a blister packaging assembly 70 (see FIGS. 3 and 4). More particularly, the blister packaging assembly 70 includes a thermoformed, blister-type PVC (polyvinyl chloride) plastic tray 72 for receiving the pre-filled applicator 10. Alternatively, the tray 72 can be made from any other suitable materials. The tray 72 includes an outer perimeter rim 74 and a compartment 76 projecting from the rim 74. The compartment 76 includes an outer cavity section 78 for receiving the distal section 24 of the barrel member 14, including the suppository product 12 pre-installed in the receptacle 40. The compartment 76 is also equipped with an intermediate cavity section 80 for receiving the intermediate section 26 of the barrel member 14. The intermediate cavity section 80 includes a pair of side extensions 82 for receiving user's fingers during the removal of the applicator 10 from the tray 72. An intermediate cavity section 84 is also connected to the intermediate cavity section 80 for receiving the proximal section 22 of the barrel member 14, while an outer cavity section 86 is connected to the intermediate cavity section 84 for receiving the thumb platform 58 of the plunger member 16. A peelable lid 88 laminated with an aluminum foil is attached to the packaging tray 72 in a conventional manner for sealing the applicator 10 in the compartment 76.

In order to use the pre-filled applicator 10 packaged in the packaging assembly 70, the applicator 10 is removed from the packaging assembly 70. The distal section 24 of the applicator 10, together with the suppository product 12 attached thereto, is then inserted into a vaginal canal (not shown) in a conventional manner. In doing so, the barrel member 14 is gripped by the user's fingers at the ribbed surface 30 of the proximal section 22. After properly placing the distal section 24 and the suppository product 12 in the vaginal canal, the thumb platform 58 of the plunger member 16 is pushed toward the distal section 24 of the barrel member 14 so as to move the barrel member 14 from its retracted position (see FIGS. 2 and 6) to its extended position (see FIGS. 5 and 7). In this regard, the applicator 10 can be held and operated by the user in any conventional manner. For instance, with the proximal section 22 of the barrel member 14 held by the user's index and middle fingers, the thumb platform 58 of the plunger member 16 can be pushed by the user's thumb. As the plunger member 16 moves from its retracted position to its extended position (as indicated by the arrow in FIG. 6), the contact platform 66 of the plunger member 16 pushes the suppository product 12 out of the receptacle 40. During the release of the suppository product 12 from the receptacle 40, the tips 44 of the petals 38 expand in a radially outward direction so as to facilitate the release of the suppository product 12. In order to ensure the release of the suppository product 12 from the applicator 10, the thumb platform 58 is pushed until the plunger member 16 is positioned in its extended position, in which the contact platform 66 is located axially outwardly from the receptacle 40 (see FIGS. 5 and 7).

After the release of the suppository product 12 from the applicator 10 into the vaginal canal, the plunger member 16 is pulled back into its retracted position so as to place the contact platform 66 within the receptacle 40. In this manner, during the removal of the applicator 10 from the vaginal cavity, the contact platform 66 is prevented from coming in contact with tissue walls of the vaginal cavity and causing injury to same. The applicator 10 is then cleaned and disinfected for subsequent use or is discarded.

It should be appreciated that the applicator 10 of the present invention provides numerous advantages over conventional applicators. For instance, because the petals 38 of the applicator 10 have a truncated construction, they are adapted to retain the suppository product 12 in the receptacle 40, while permitting easy release of same from the receptacle 40. As a result, the suppository product 12 can be released from the applicator 10 in response to the application of an axial force that is significantly less than the force required for conventional applicators. In this manner, even if the suppository product 12 sticks to the interior surface of the receptacle 40 during its storage or insertion into a bodily cavity, it can be released from the receptacle 40 without significant difficulty. Because of its ability to release the suppository product 12 stuck to the receptacle 40, the applicator 10 can be provided to users in pre-filled and packaged form.

The oversized contact platform 66 of the plunger member 16 further ensures the proper dispensing of the suppository product 12 from the receptacle 40. For instance, because of its large size, the contact platform 66 tends to apply an axial force evenly to the suppository product 12, thereby minimizing distortion of the suppository product 12 during its release from the receptacle 40. Moreover, the contact platform 66 functions to strip the suppository product 12 off the interior surface of the receptacle 40 if there is excess friction or sticking between the suppository product 12 and the barrel member 14. In addition, because the suppository product 12 is mounted to the flaring distal section 24, the remaining sections of the barrel member 14 (i.e., the intermediate and proximal sections 26, 22) can be made relatively slender.

It should be noted that the applicator 10 of the present invention can have numerous modifications and variations. For instance, the applicator 10 can be provided with a different number of petals 38. Moreover, although the present invention is especially suitable for use in delivering suppository products to vaginal canals or cavities, it can be used to dispense suppository products or other pharmacological products in other body cavities such as a rectum. Further, the applicator 10 can be modified to accommodate suppository products having different geometrical shapes. In addition, the petals 38 can be provided with different shapes and lengths. The applicator 10 can also be packaged in different types of packages.

FIGS. 8–19 depict additional exemplary embodiments of the present invention. Elements illustrated in FIGS. 8–13, FIGS. 14–15A, FIG. 16, FIG. 17, FIGS. 18–18B and FIG. 19, which correspond to the elements described above with reference to FIGS. 1–7, have been designated by corresponding reference numbers increased by one hundred, two hundred, three hundred, four hundred, five hundred and six hundred, respectively. Unless otherwise stated or illustrated, the exemplary embodiments of FIGS. 14–19 are constructed, used and operated in the same basic manner as the exemplary embodiment shown in FIGS. 1–7.

With reference to FIGS. 8, 9, 12 and 13, there is shown a suppository applicator 110 constructed in accordance with the second embodiment of the present invention. The applicator 110, which is adapted for use in delivering an oval-shaped suppository product 112 to a bodily cavity (e.g., a vaginal orifice), includes a barrel member 114 having an open proximal end 128 and an open distal end 134. Unlike the barrel member 14 of the embodiment of FIGS. 1–7, the entire barrel member 114 is substantially cylindrical in shape and is slightly tapered as it extends from the proximal end 128 to the distal end 134 (i.e., the diameter of the proximal end 128 is slightly greater than that of the distal end 134). As a result, the distal end 134 of the barrel member 114 is not flared. The barrel member 114 includes an interior passageway 118 extending between the proximal and distal ends 128, 134. A perimeter rim wall 190 is formed at the proximal end 128, while an annular retaining rib 192 is formed in the passageway 118 adjacent the proximal end 128. Flexible, truncated petals 138 are also formed at the distal end 134 of the barrel member 114. The petals 138 cooperate with one another so as to define a receptacle 140 for receiving the suppository product 112.

Still referring to FIGS. 8, 9, 12 and 13, the applicator 110 also includes a plunger member 116 having a single-piece construction. More particularly, the plunger member 116 includes a ribbed shaft 150, a proximal end 152 and a distal end 154. A thumb platform 158 is formed at the proximal end 152 for engagement with the rim wall 190 of the barrel member 114, while a contact platform 166 is formed at the distal end 154. The contact platform 166 has a diameter smaller than the inner diameter of the retaining rib 192 of the barrel member 114 such that it can be inserted into the passageway 118. The diameter of the contact platform 166 is also larger than an inner diameter D (see FIG. 8) of the receptacle 140 defined by the petals 138 such that, when the contact platform 166 is positioned in the receptacle 140, it comes in contact with the petals 138 and causes same to flex radially outwardly (see FIG. 13), thereby facilitating the release of the suppository product 112 from the receptacle 140. A stopping platform 194 is formed on the shaft 150 adjacent to the proximal end 152 of the shaft 150. The stopping platform 194 has a diameter slightly larger than the inner diameter of the retaining rib 192 of the barrel member 114 for purposes to be discussed hereinafter. In this regard, the stopping platform 194 is slightly flexible such that it can be inserted into the passageway 118 from the proximal end 128 of the barrel member 114 and positioned between the retaining rib 192 and the distal end 134.

The plunger member 116 is movably mounted in the passageway 118 of the barrel member 114. As a result, the plunger member 116 is movable relative to the barrel member 114 between a retracted position (see FIG. 12), in which the contact platform 166 is located remote from the petals 138, and an extended position, in which the contact platform 166 is in contact with the petals 138 (see FIG. 13). In this regard, the retaining rib 192 of the barrel member 114 is engageable with the stopping platform 194 of the plunger member 116 so as to inhibit the plunger member 116 from moving beyond its retracted position. Similarly, the rim wall 190 of the barrel member 114 is adapted to engage the thumb platform 158 of the plunger member 116 for the purpose of inhibiting it from moving beyond its extended position.

Figure 10:
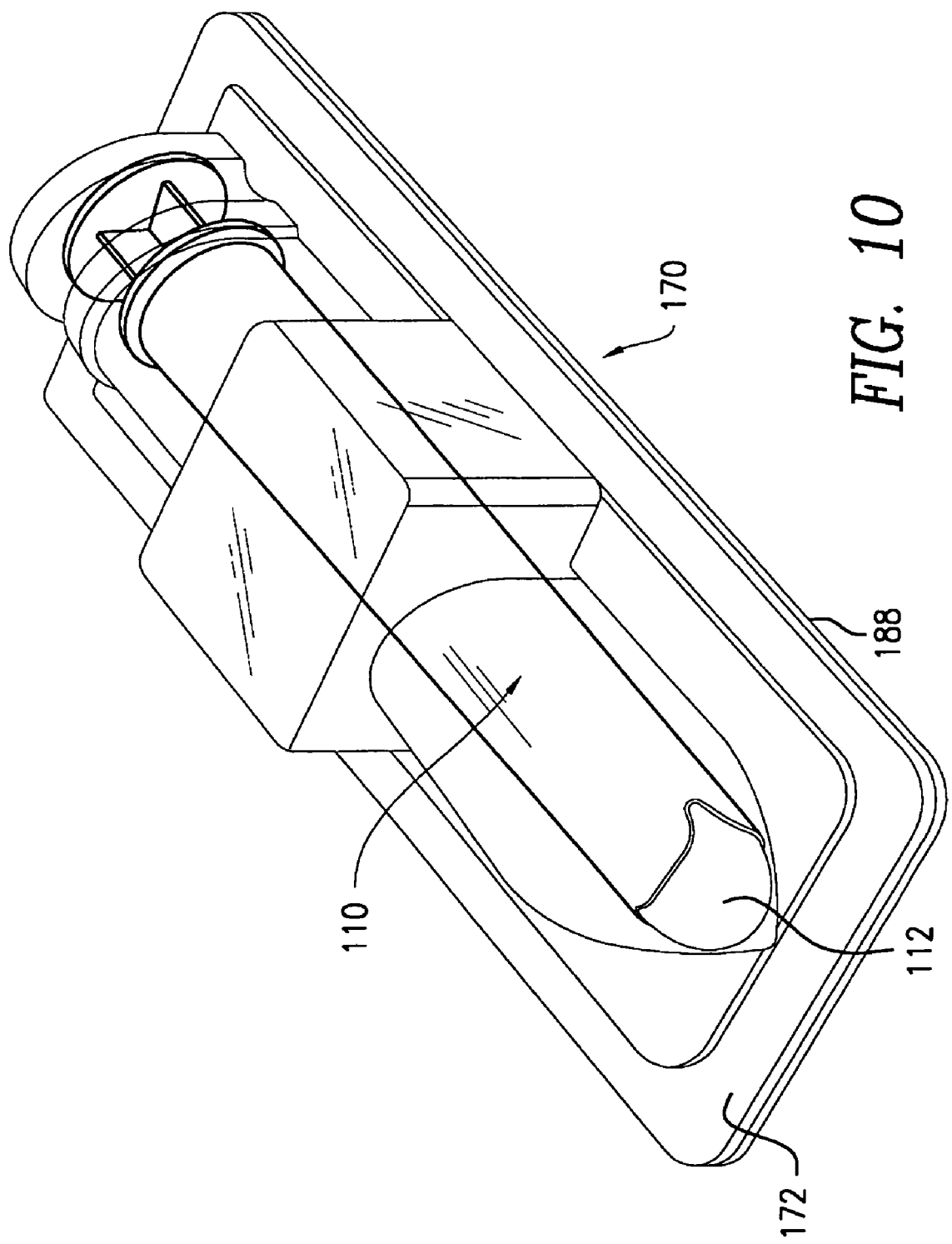
FIG. 10 is a perspective view of the applicator of FIG. 9 packaged in a blister packaging assembly.
Figure 11:
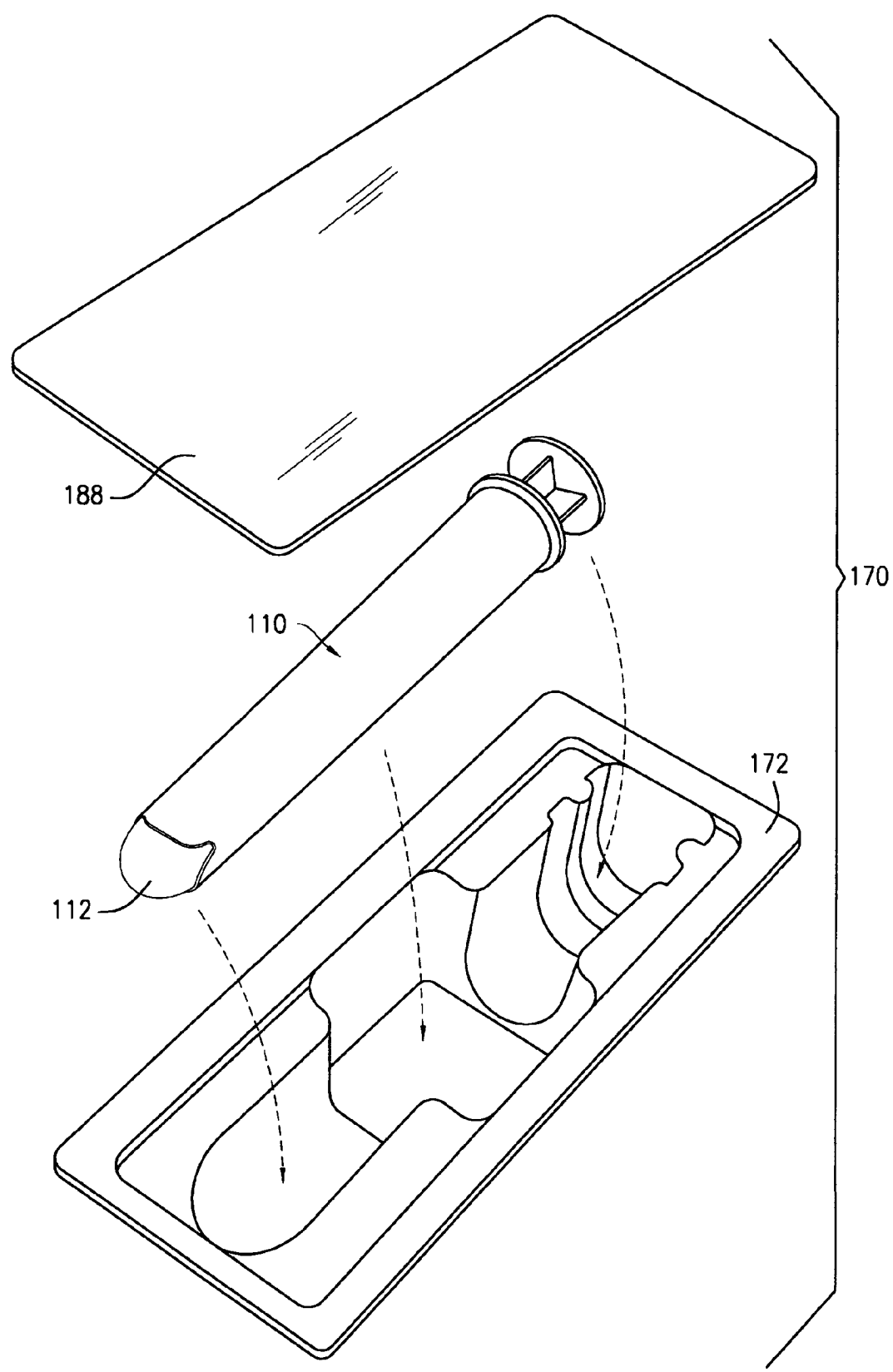
FIG. 11 is an exploded perspective view of the blister packaging assembly of FIG. 10.

With reference to FIGS. 10 and 11, a blister packaging assembly 170 is provided for packaging the applicator 110 pre-filled with the suppository product 112. More particularly, the packaging assembly 170 has a construction basically identical to that of the blister packaging assembly 70 of the embodiment shown in FIGS. 1–7. For instance, the packaging assembly 170 has a tray 172 for receiving the pre-filled applicator 110 and a peelable lid 188 attached to the tray 172.

Figure 14:
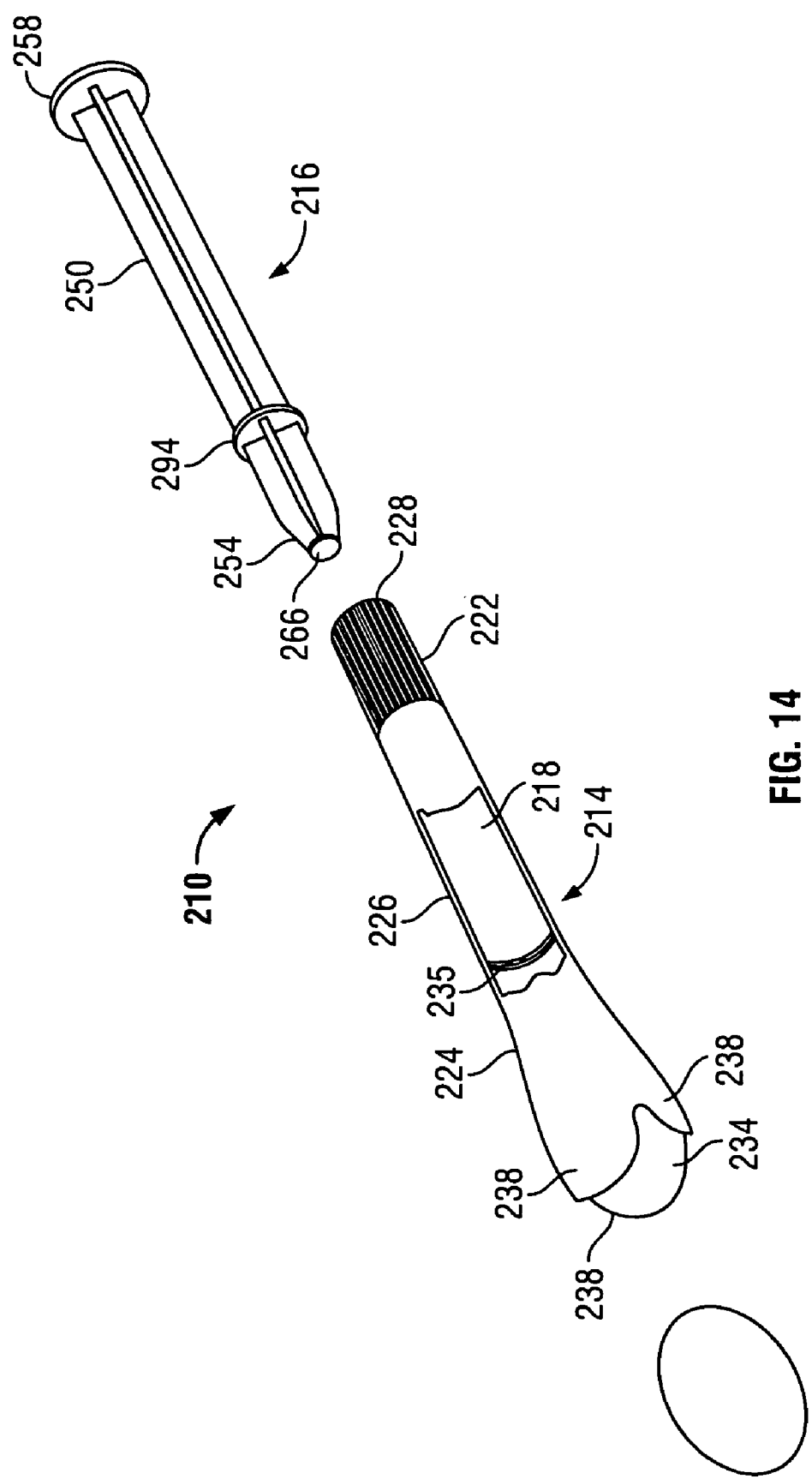
FIG. 14 is an exploded perspective view of an applicator constructed in accordance with a third embodiment of the present invention.
Figure 15:
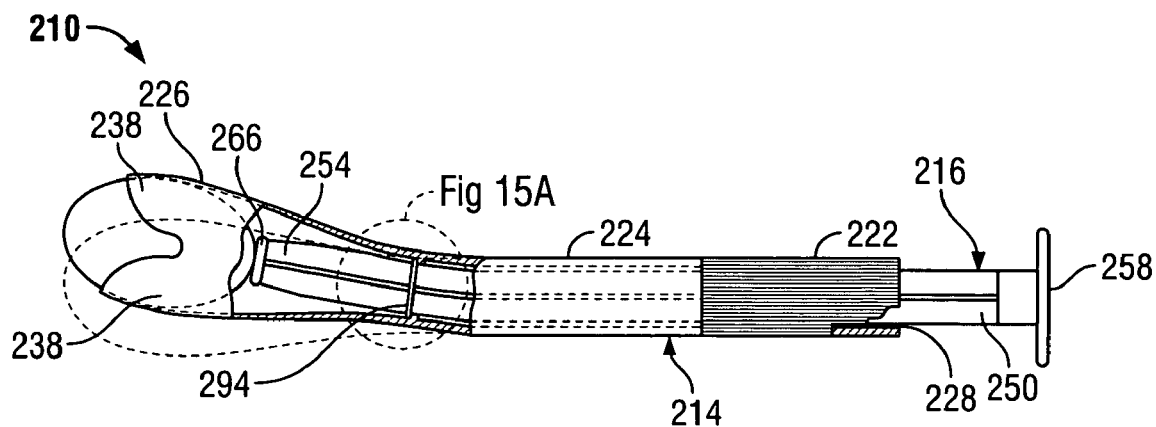
FIG. 15 is a partially broken-away, side elevational view of the applicator shown in FIG. 14.
Figure 15A:
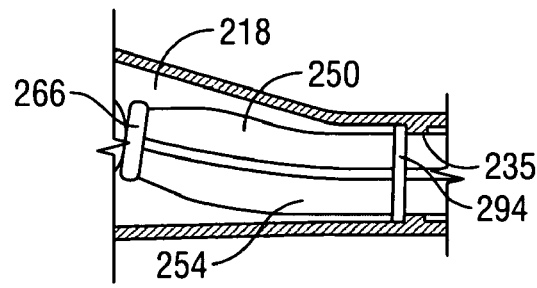
FIG. 15A is an enlarged view of a portion of the applicator shown in FIG. 15.

FIGS. 14–15A illustrate an applicator 210 constructed in accordance with a third embodiment of the present invention for delivering suppositories into bodily cavities, such as vaginal cavities or recta. Unless stated otherwise, the applicator 210 has a construction and operation basically identical to the construction and operation of the applicator 10 of the embodiment shown in FIGS. 1–7. More particularly, the applicator 210 includes a barrel member 214 having a proximal section 222, a distal section 224 and an intermediate section 226. More particularly, the proximal section 222 has an open end 228, while the distal section 224 has an open end 234 and flexible, truncated petals 238. An interior passageway or bore 218 extends through the barrel member 214 from the open end 228 of the proximal section 222 to the open end 234 of the distal section 224. An annular ring 235 also projects from an interior wall of the barrel member 214 into the passageway 218.

Referring to FIGS. 14 and 15, the barrel member 214 is made, in its entirety (including the proximal, distal and intermediate sections 222, 224, 226), from a substantially flexible material such that it is readily bendable or deformable so as to conform to an interior wall and/or contour of a bodily cavity when inserted therein. More particularly, while the barrel member 214 can be made from any flexible or elastic materials, thermoplastic elastomers, such as styrene-ethylene-butylene copolymers, flexible polyvinyl chloride modified with plasticizers, ultra-low density polyethylene and silicone are especially suitable for use in making the barrel member 214. Various durometer can be used to achieve the desired degree of flexibility of the barrel member 214. The barrel member 214 can also be made from a rigid or semi-rigid material (e.g., low density polyethylene) and be constructed with a substantially thin wall such that it is provided with a high degree of flexibility. Any conventional processes can be utilized to make the barrel member 114. For instance, the barrel member 114 can be injection-molded or extruded from a flexible material.

Still referring to FIGS. 14 and 15, a plunger member 216 movably extends through the passageway 218 of the barrel member 214. The plunger member 216 includes a ribbed shaft 250 and a thumb platform 258 which are monolithically formed with one another. Referring to FIGS. 15 and 15A, the shaft 250 has a tapered distal end 254, while a disc 266 is attached to the distal end 254 of the shaft 250. More particularly, the disc 266 has a size smaller than the diameter of the passageway 218 or the inner diameter of the annular ring 235 of the barrel member 214 such that it can pass through the passageway 218 of the distal, proximal and intermediate sections 222, 224, 226 of the barrel member 214. In this manner, the plunger member 216, which has a monolithic construction, can be inserted into the barrel member 214 from its proximal section 222. As a result, the plunger member 216 can be assembled with the barrel member 214 in a single step (i.e., the step for attaching the thumb platform 258 to the shaft 250 is omitted), thereby facilitating the assembly of the applicator 210. The disc 266 is also sized and shaped such that it can engage and expel a suppository loaded in the applicator 210 without puncturing same.

Like the plunger member 16 of the embodiment shown in FIGS. 1–7, the shaft 250 is adapted to frictionally engage the annular ring 235 such that it is slidably griped by same to create a frictional fit between the barrel member 214 and the plunger member 216. The plunger member 216 is also provided with a disc 294 mounted to the shaft 250. The disc 294 is positioned and is sized and shaped such that it functions as the stopping platform 194 of the embodiment illustrated in FIGS. 8–13. More particularly, the disc 294 has a diameter slightly larger than the inner diameter of the annular ring 235 of the barrel member 214. As a result, when the plunger member 216 is properly inserted into the passageway 218 of the barrel member 214, the disc 294 is engageable with the annular ring 235 so as to inhibit the plunger member 216 from moving beyond its retracted position (see FIG. 15A) and hence retains the plunger member 216 assembled with the barrel member 214.

Like the barrel member 214, the plunger member 216 can be from a similar flexible material in a conventional manner such that it is bendable or deformable together with the barrel member 214 when the applicator 210 is inserted into a vaginal cavity. Alternatively, the plunger member 216 can be made from a conventional rigid or semi-rigid material (e.g., semi-rigid thermoplastic material, such as polyethylene or plastic). Because of its ribbed shaft 250, the barrel member 216 is relatively flexible even if it is made from a rigid or semi-rigid material. In such circumstances, the flexible barrel member 214 assembled with the relatively rigid plunger member 216 can provide the applicator 210 with flexibility sufficient for its intended use and purpose.

The applicator 210 is used in the same basic manner as the applicator 10 of the embodiment shown in FIGS. 1–7. The applicator 210 normally assumes a straight or linear shape (as indicated by the broken line representation of the applicator 210 in FIG. 15). When the applicator 210 is inserted into a bodily cavity, such as a vaginal canal, because of its flexibility, it can bend freely and/or readily (as indicated by the solid line representation of the applicator 210 in FIG. 15) so as to conform in shape to natural curves and other possible obstructions in the vaginal canal, thereby accommodating variations in anatomy and hence providing enhanced conform to the user. Due to its flexibility, the applicator 210 also allows the user to dispense a suppository in positions other than the conventionally recommended horizontal "missionary" position (e.g., in a standing or squatting position with the user's knees slightly bent). When the applicator 210 is removed from the vaginal cavity, it returns to its normally straight shape.

Besides the advantages discussed above, the applicator 210 has numerous additional advantages. For instance, because the applicator 210 is made from a flexible material, it provides a soft feel to the user. Moreover, because the truncated petals 238 are made from a flexible material, they open easily upon loading a suppository into the applicator 210 and upon dispensing same from the applicator 210.

The applicator 210 can have numerous modifications and variations. For instance, the barrel member 214 and/or the plunger member 216 can be constructed such that certain portions are flexible, while the remaining portions are rigid. By way of example, the distal section 224 of the barrel member 214, including the petals 238 which define a suppository receptacle, can be made from a rigid material, such as polyethylene, while the rest of the barrel member 214 (i.e., the proximal and intermediate sections 222, 226) can be separately extruded or injection-molded from a flexible material. The relatively rigid distal section 224 can then be attached to the flexible intermediate section 226 to form the barrel member 214. More particularly, the distal section 224 can be provided with a cylindrically shaped projection which can be friction-fitted into or onto the intermediate section 226. A rigid flange (having a construction similar to the construction of the flange 190 of the embodiment shown in FIGS. 8–13) can also be formed separately and be attached to the open end 228 of the proximal section 222 of the barrel member 214 (e.g., the rigid flange can be provided with a cylindrically shaped projection which can be friction-fitted into or onto the open end 228 of the barrel member 214).

Figure 16:
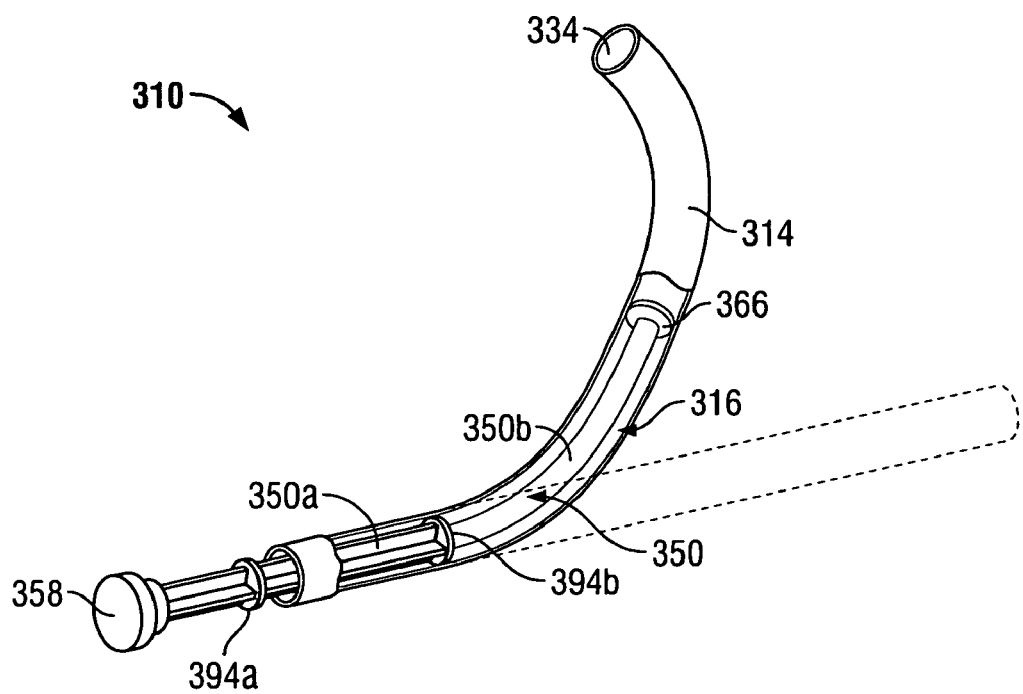
FIG. 16 is a partially broken-away, perspective view of an applicator constructed in accordance with a fourth embodiment of the present invention.

FIG. 16 shows an applicator 310 constructed in accordance with a fourth embodiment of the present invention.

Unless stated or illustrated otherwise, the applicator 310 has a construction and operation basically identical to the applicator 210 of the embodiment shown in FIGS. 14–15A. The applicator 310 includes a tube or barrel member 314 which is made from a flexible material. Unlike the barrel member 214 of the embodiment of FIGS. 14–15A, the barrel member 314 is not provided with any petals, but includes an open end 334 for receiving suppositories or other medicated solid or non-solid materials (e.g., creams and ointments).

The applicator 310 also includes a plunger member 316 having a shaft 350 which is equipped with a ribbed section 350a and a round rod section 350b. The plunger member 316 also has a disc 366 mounted to an end of the round rod section 350b for expelling the materials loaded in the open end 334 of the barrel member 314, and a pair of discs 394a, 394b. The disc 394a is mounted on the ribbed section 350a, while the disc 394b is mounted to the plunger member 316 at the interface between the ribbed and round rod sections 350a, 350b. The discs 394a, 394b are adapted to be inserted into the passageway of the barrel member 314 and engage the inner cylindrical surface of the barrel member 314 for providing a relatively loose friction fit between the barrel member 314 and the plunger member 316. The plunger member 316, which can be made from a flexible material or a rigid or semi-rigid material, has a thumb platform 358. Alternatively, the platform 358 can be replaced with other types of mechanisms, such as a ring attached to the plunger member 316 for accommodating or receiving a person's thumb or finger.

The applicator 310 normally assumes a linear or straight shape (as indicated by the broken line representation of the applicator 310 in FIG. 16). Because the barrel member 314 and/or the plunger member 316 are flexible, the applicator 310 is adapted to readily bend or deform (as indicated by the solid line representation of the applicator 310 in FIG. 16) so as to conform to the natural anatomy or contour of a bodily cavity into which the applicator 310 is inserted.

Figure 17:
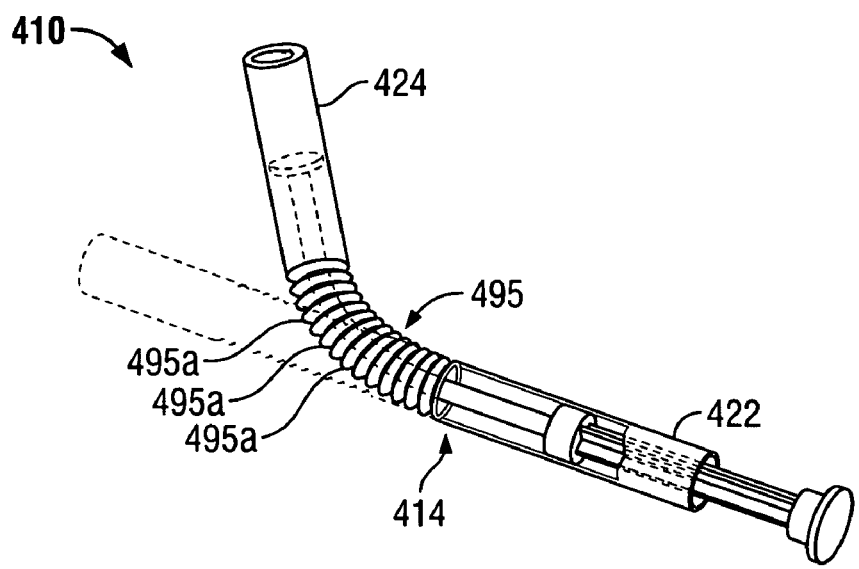
FIG. 17 is a partially broken-away, perspective view of an applicator constructed in accordance with a fifth embodiment of the present invention.

FIG. 17 illustrates an applicator 410 constructed in accordance with a fifth embodiment of the present invention for dispensing medicated solid materials (e.g., suppositories) and/or medicated non-solid materials (e.g., creams and ointments). More particularly, the applicator 410 includes a tube or barrel member 414 having a pair of rigid or semi-rigid end sections 422, 424 and a bellow section 495 mounted between the end sections 422, 424. The bellow section 495 has a plurality of bellows 495a made from a rigid material, but formed with a relatively thin wall, such that the barrel member 414 is bendable about the bellow section 495. The bellow section 495 can be located in any position in the barrel member 414 where shape change is desired. More than one bellow sections can also be provided in the barrel member 414.

Figure 18:
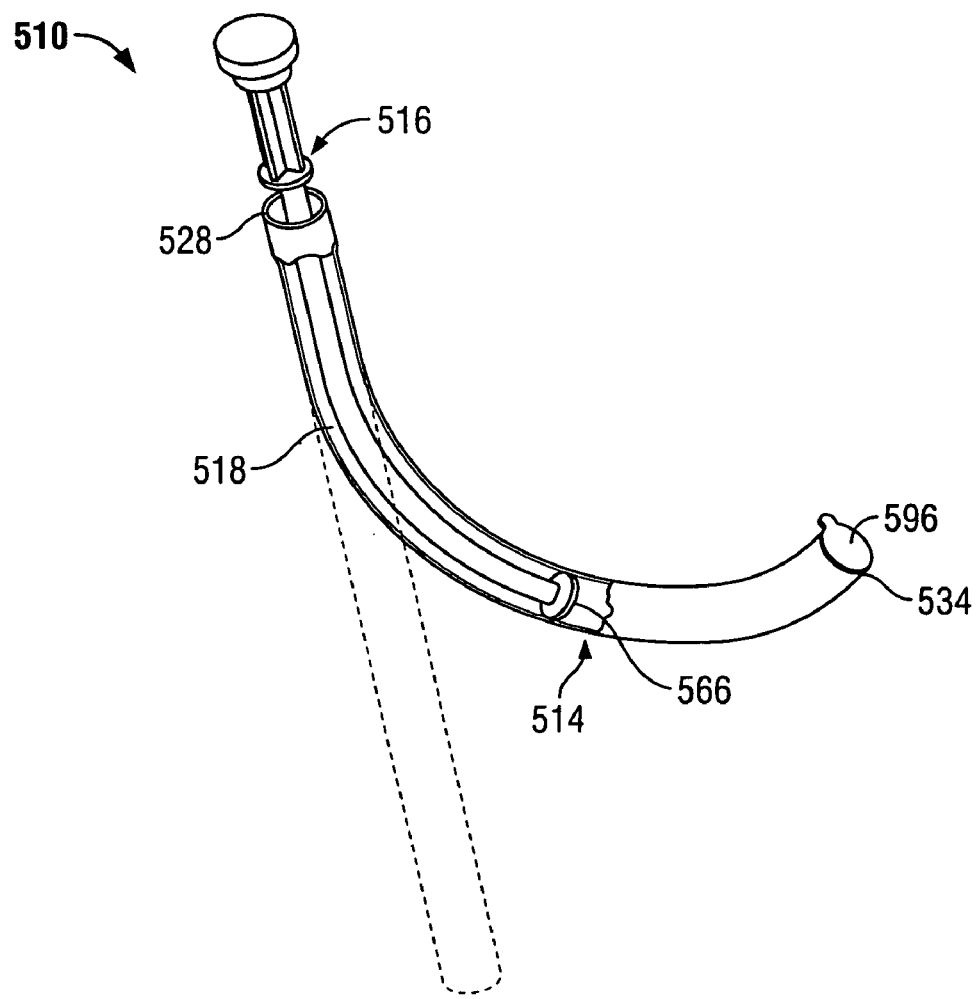
FIG. 18 is a partially broken-away, perspective view of an applicator constructed in accordance with a sixth embodiment of the present invention.

Now referring to FIG. 18, there is shown an applicator 510 constructed in accordance with a sixth embodiment of the present invention for dispensing medicated non-solid materials, such as creams or ointments. More particularly, the applicator 510 includes a tube or barrel member 514 made from a flexible material such that the barrel member 514 is readily deformable from a normally straight shape to a bent shape. The barrel member 514 has a pair of ends 528, 534 and a passageway 518 extending therebetween. A peel-off foil 596 (see also FIG. 18A) is attached to the end 534 of the barrel member 514 and seals same so as to contain non-solid medicated materials pre-filled in the passageway 518. The foil 596 can be peeled off from the barrel member 514 prior to the insertion of the applicator 510 into a vaginal cavity. Alternatively, other types of closure members can be used for sealing the end 534 of the barrel member 514. For instance, a twist-off cap or tip 596a (see FIG. 18B) can be removably attached to the end 534 of the barrel member 514.

The applicator 510 is also provided with a plunger member 516 having a disc 566. More particularly, the disc 566 forms an air or liquid-tight seal with the interior wall of the barrel member 514 so as to contain medicated creams or ointments pre-filled in the passageway 518 and to dispense same from the barrel member 514 when the plunger member 516 is moved from its retracted position to its extended position.

FIG. 19 shows an applicator 610 constructed in accordance with a seventh embodiment of the present invention for dispensing medicated non-solid materials into a bodily cavity. More particularly, the applicator 610 includes a barrel member 614 having a distal section 624 and a proximal section 622 that are securely attached to one another. The distal section 624 is made, in its entirety, from a flexible material, while the proximal section 622 is made, in its entirety, from a rigid or semi-rigid material. The proximal section 622 has a distal end 697 inserted into the distal section 624 and secured thereto by a friction or interference fit. Alternatively, the distal end 697 of the proximal section 622 can be permanently attached to the distal section 624 by other mechanisms (e.g., bonding or gluing). The distal section 624 has a slightly angled, tapered tip 698 which is configured so as to reduce friction and/or resistance against the vaginal tissue of a vaginal cavity, thereby facilitating the insertion of the applicator 610 into the vaginal cavity and hence promoting additional comfort to the user. The applicator 610 is also equipped with a plunger member 616, which can have a one-piece or multiple-piece construction.

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined by the appended claims.

The invention claimed is:

1. An assembly comprising a pharmaceutical product; and a device for delivering said pharmaceutical product to a bodily cavity, said device including a barrel member having a distal end, which includes an opening, a proximal end, which is positioned opposite said distal end, and a plurality of petals extending outwardly from said distal end in a generally axial direction, said petals cooperating with said opening so as to form a receptacle in said distal end of said barrel member for releasably receiving said pharmaceutical product, each of said petals including a base connected to said distal end of said barrel member and terminating at a truncated flexible tip, each of said petals including an intermediate section extending between a corresponding one of said bases and a corresponding one of said tips, each of said petals being sized and shaped such that the entire portion of each of said intermediate sections is spaced from said pharmaceutical product in a radially outward direction and such that only said tips engage said pharmaceutical product at a substantially central portion thereof when said pharmaceutical product is fully received in said receptacle, whereby a large section of the pharmaceutical product extends outwardly beyond said petals so as to facilitate the release of said pharmaceutical product from said receptacle, said tips of said petals forming a second opening that maintains a larger diameter than the smallest inner diameter along the length of said barrel member both before and after release of said pharmaceutical product, said barrel member having at least one substantially flexible section located between said distal end and said proximal end such that said barrel member is bendable about said at least one flexible section.

2. The assembly of claim 1, wherein said at least one flexible section is made from a substantially flexible material.

3. The assembly of claim 2, wherein said barrel member is made, in its entirety, from a substantially flexible material.

4. The assembly of claim 1, wherein said opening is encircled by said petals.

5. The assembly of claim 4, wherein each of said petals is flexible such that said tips are expandable and contractible in said radially outward direction.

6. The assembly of claim 3, wherein said flexible material is selected from a group consisting of a thermoplastic elastomer and a silicone.

7. The assembly of claim 6, wherein said thermoplastic elastomer is selected from the group consisting of a styrene ethylene butylenes copolymer, flexible polyvinyl chloride modified with plasticizers and ultra-low density polyethylene.

8. The assembly of claim 1, wherein said barrel member has at least one substantially rigid section located between said distal end and said proximal end such that said at least one rigid section is movable relative to said at least one flexible section.

9. The assembly of claim 8, wherein said at least one rigid section includes first and second sections, said at least one flexible section being located between said first and second sections such that said first section is movable relative to said second section.

10. The device of claim 9, wherein said at least one flexible section includes a bellow section having a plurality of bellows positioned between said first and second sections of said barrel member.

11. The assembly of claim 1, further comprising a plunger member having at least one substantially flexible section such that said plunger member is bendable about said at least one flexible section thereof.

12. The assembly of claim 11, wherein each of said barrel member and said plunger member is made, in its entirety, from a flexible material.

13. The device of claim 1, wherein said plunger member is made, in its entirety, from a non-flexible material.

14. The device of claim 1, wherein said barrel member is sized and shaped so as to receive a non-solid medicated product.

15. The device of claim 14, wherein said non-solid medicated product includes a medicated cream or ointment.

16. The device of claim 15, further comprising sealing means for releasably sealing said opening of said barrel member so as to contain said non-solid product in said barrel member.

17. The assembly of claim 1, wherein said barrel member is sized and shaped so as to receive a solid medicated product.

18. The assembly of claim 1, wherein said petals are sized and shaped such that approximately half of said pharmaceutical product received in said receptacle extends outwardly beyond said tips.

19. A device for delivering pharmaceutical products or the like to a bodily cavity, comprising a barrel member having a dispensing end, which includes an opening, a proximal end, which is located opposite said dispensing end, a first section which extends from said proximal end and which has an end remote from said proximal end of said barrel member, and a second section, which extends from said end of said first section in a generally axial direction and terminates at said dispensing end of said barrel member, said barrel member having a first diameter at an interface between said first and second sections and a second diameter at said dispensing end of said barrel member, said second section having a flared shape such that said second diameter is greater than said first diameter, said barrel member having a plurality of petals extending outwardly from said dispensing end in said axial direction, said petals cooperating with said opening so as to form a receptacle in said dispensing end of said barrel member releasably receiving a pharmaceutical product, each of said petals having a truncated flexible tip, said petals curving inwardly in a generally radial direction as they extend in said axial direction from said dispensing end of said barrel member to said tips, and said tips sized and shaped so as to engage a substantially central portion of the pharmaceutical product such that when the pharmaceutical product is fully received in said receptacle, a large section of the pharmaceutical product extends outwardly beyond said petals so as to facilitate the release of a pharmaceutical product received in said receptacle, and wherein said tips of said petals form a second opening that maintains a larger diameter than the first diameter at the interface between said first and second sections both before and after release of said pharmaceutical product, said barrel member having at least one substantially flexible section located between said dispensing end and said proximal end such that said barrel member is bendable about said at least one flexible section.

20. The device of claim 19, wherein said petals engage a pharmaceutical product only at said tips when the pharmaceutical product is fully inserted into said receptacle.

* * * * *